(12) United States Patent
Brost

(10) Patent No.: US 12,301,547 B2
(45) Date of Patent: *May 13, 2025

(54) METHOD AND APPARATUS FOR DATA COMMUNICATION IN A NETWORK

(71) Applicant: Siemens Healthineers AG, Forchheim (DE)

(72) Inventor: Alexander Brost, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,358

(22) Filed: Feb. 13, 2024

(65) Prior Publication Data
US 2024/0187384 A1    Jun. 6, 2024

Related U.S. Application Data

(63) Continuation of application No. 17/012,136, filed on Sep. 4, 2020, now Pat. No. 11,936,626.

(30) Foreign Application Priority Data

Sep. 11, 2019    (EP) .................................... 19196763

(51) Int. Cl.
*H04L 9/40*    (2022.01)
*G06F 21/62*    (2013.01)
(Continued)

(52) U.S. Cl.
CPC ...... *H04L 63/0421* (2013.01); *G06F 21/6254* (2013.01); *G16H 30/20* (2018.01);
(Continued)

(58) Field of Classification Search
CPC . H04L 63/0421; H04L 67/12; H04L 63/0807; H04L 67/10; H04L 67/51;
(Continued)

(56) References Cited

U.S. PATENT DOCUMENTS 10,452,812 B2 *  10/2019  Gogin .................... G16H 30/40
11,366,927 B1 *   6/2022  Chandrasekaran .... G16H 10/60
(Continued)

FOREIGN PATENT DOCUMENTS

| CN | 101422002 A | 4/2009 |
| CN | 108431817 A | 8/2018 |
| WO | WO-2013/123085 A1 | 8/2013 |

OTHER PUBLICATIONS

Wikipedia "De-identification" Jul. 20, 2019 https://en.wikipedia.org/w/index.php?title=Deidentification&oldid=907090769.
Extended European Search Report dated Mar. 17, 2020.

*Primary Examiner* — Mohammed Waliullah
(74) *Attorney, Agent, or Firm* — Harness, Dickey & Pierce, P.L.C.

(57) ABSTRACT

A method is for data communication in a network including a first network area and a second network area. The method includes provisioning medical patient data; provisioning identification data for identification of a patient; provisioning a code linked to the identification data; sending medical patient data and the code from the first network area to a server in the second network area; and processing the patient data by the server. The method further includes provisioning identification data or input of identification data for identification of a patient by the user; establishing of a code linked to the identification data; automatic sending of the code to the server; establishing the status of the processing patient data linked to the code; creating a corresponding status notification by the server; and sending the status notification to the user.

21 Claims, 5 Drawing Sheets

(51) Int. Cl.
*G16H 30/20* (2018.01)
*G16H 40/20* (2018.01)
*G16H 50/20* (2018.01)
*H04L 67/12* (2022.01)

(52) U.S. Cl.
CPC ............. *G16H 40/20* (2018.01); *G16H 50/20* (2018.01); *H04L 67/12* (2013.01)

(58) Field of Classification Search
CPC .... G06F 21/6254; G16H 30/20; G16H 40/20; G16H 50/20; G16H 10/60
See application file for complete search history.

(56) References Cited

U.S. PATENT DOCUMENTS

| | | |
|---|---|---|
| 2002/0010679 A1 | 1/2002 | Felsher |
| 2007/0237108 A1 | 10/2007 | Baard |
| 2009/0112882 A1 | 4/2009 | Maresh et al. |
| 2013/0208966 A1* | 8/2013 | Zhao ...................... G06Q 40/08 709/219 |
| 2015/0356257 A1* | 12/2015 | Wright ................... G16H 40/20 705/2 |
| 2016/0147945 A1* | 5/2016 | MacCarthy ........... H04W 12/02 705/51 |
| 2017/0177798 A1* | 6/2017 | Samuel ................... H04L 67/12 |
| 2018/0256042 A1 | 9/2018 | Beckers et al. |

* cited by examiner

METHOD AND APPARATUS FOR DATA COMMUNICATION IN A NETWORK

PRIORITY STATEMENT

The present application is a continuation of U.S. patent application Ser. No. 17/012,136, filed Sep. 4, 2020, which claims priority under 35 U.S.C. § 119 to European patent application number EP 19196763.7 filed Sep. 11, 2019, the entire contents of each of which are hereby incorporated herein by reference.

FIELD

Embodiments of the invention generally relate to a method and an apparatus for data communication in a network as well as to a system for data communication.

BACKGROUND

The use of artificial intelligence ("AI") is becoming ever more important in the medical community. Within the context of medicine, AI algorithms deliver additional information that was previously either not available or required time to be spent by a medically-trained person to obtain it. AI algorithms as a rule require high-performance computing, so that it is mostly advantageous to provide them as an external service, e.g. in the form of a cloud environment.

In this case however the problem that occurs is that many medical establishments do not wish to have any results generated by an AI algorithm directly in their PACS or RIS (or EMR) and, after patient data has been processed by an AI algorithm, initially demand that it be checked by a human being. In this context RIS is the abbreviation for Radiology Information System, PACS for Picture Archiving and Communication System and EMR for Electronic Medical Record. A frequently used standard for the data format is the DICOM (DICOM=Digital Imaging and Communications in Medicine) standard.

As regards the data, this is frequently available in the network environment of a medical establishment as PHI data (PHI: Patient Health Information), which means that patient names are linked to the data, i.e. direct conclusions can be drawn about the state of the patients' health. The opposite of this is NoPHI data (anonymized data), which does not allow any direct link back to a patient. For legal reasons it is often the case that no PHI data may be sent to an external service (e.g. a cloud service), at least not when this cloud service is connected via a public network, such as via the Internet for example. A network in which no PHI data may be processed will be referred to below as a NoPHI network to differentiate it from a medical network, which is seen as a PHI network, where PHI data may be processed. The Internet is a NoPHI network for example.

SUMMARY

In order to solve the problem of transfer to a PACS or to another medical system, providers of AI services have implemented dedicated user interfaces for example, in order to confirm the results and reject them. However, the inventors have discovered that this requires that a user (medical specialist) logs in manually at the AI system in order to check the results. The user does not know in such cases whether any AI results are available at all. Since data must be stored anonymized in the cloud (at least if it is accessible via a NoPHI network), the doctor cannot identify a patient directly.

At least one embodiment of the present invention specifies an alternate, more convenient method and a corresponding apparatus for data communication in a network, as well as a system for data communication, with which the disadvantages described above can be avoided.

Embodiments of the present invention are directed to various methods, an apparatus, a system, and also a medical system.

An embodiment of the inventive method is used for data communication in a network, wherein this network comprises a first network area (this is a medical network area or a PHI network) and a second network area (this is a NoPHI network area, e.g. the Internet), to which, according to specification, patient data is sent anonymized. In the first (medical) network area patient data can be present as PHI data, since, according to specification, medical standards should apply there. In an embodiment, the method comprises:

Provision of medical patient data,
Provision of identification data for identifying the patient, and
Provision of a code, which is linked to the identification data.

An inventive (user-side) method of at least one embodiment for data communication in a network with a first network area and a second network area, to which, according to specification, patient data is sent anonymized, can work hand-in-hand with the server-side method described below. So that data is processed anyway and a corresponding notification can be created anyway, the following steps should be performed beforehand:

Provision of medical patient data,
Provision of identification data for identification of a patient,
Provision of a code, which is linked to the identification data,
Sending of medical patient data and the associated code from the first network area to a server in the second network area (and naturally processing of the patient data by the server).

The (user-side) method of at least one embodiment comprises the following steps:

Provision of identification data or input of identification data for identification of a patient by a user,
Establishing of a code linked to this identification data,
Automatic sending of the code to the server,
Receiving of a status notification of the server and forwarding of the status notification to the user.

An inventive (server-side) method of at least one embodiment for data communication in a network with a first network area and a second network area, to which, according to specification, patient data is sent anonymized, which can work hand-in-hand with the user-side method stated above, comprises the following steps:

Receiving of medical patient data and an associated code from the first network area by a server in the second network area,
Processing of the patient data (which has been sent above to the server) by the server,
Receiving of a code sent by a user by the server,
Establishing of the status of the processing of patient data linked to this code, and creation of a corresponding status notification by the server, and
Sending of the status notification to the user.

The inventive apparatus of at least one embodiment is used for data communication in a network with a first (medical) network area and a second (NoPHI) network area, to which, according to specification, patient data is sent anonymized. In this case communication is based on medical patient data, identification data for identification of the patient and a code linked to the identification data. The apparatus comprises the following components:

- an input interface designed for entry of identification data for identification of a patient by a user. This can be a keyboard for example, but can also be a terminal.
- an identification unit designed for establishing a code linked to this identification data. This identification unit should have access to that component, which creates a code from identification data or a module for creating a code from identification data as described above within the framework of the method.
- a data interface designed for sending the code to the server (e.g. the cloud service). This can be a normal, well-known data interface, in particular such as is used for communication from a medical network.
- a data interface designed for receiving a status notification of the server (e.g. of the cloud service) and for forwarding the status notification to the user. This can be a normal, well-known data interface, in particular such as is used for communication from a medical network. In particular it is the same data interface as that described above, which is designed for bidirectional communication.

A corresponding inventive server system of at least one embodiment for data communication in a network with a first network area and a second network area, to which, according to specification, patient data is sent anonymized, which can work hand-in-hand with the (user-side) method stated above, comprises the following components:

Receiving of medical patient data and an associated code from the first network area sent to a server in the second network area, Processing of the patient data (which has been sent above to the server) by the server, Receiving by the server of a code sent by a user, Establishing of the status of processing of patient data linked to this code, and creation of a corresponding status notification by the server, and Sending of the status notification to the user.

An inventive system of at least one embodiment for data communication comprises the following components:

- a network comprising a first (medical) network area and a second (NoPHI) network area, to which, according to specification, patient data is sent anonymized.
- a unit designed for provision of medical patient data, of identification data for identification of the patient. This unit can be a PACS or a medical imaging system and/or an RIS for example.
- a unit designed for provision of a code, which is linked to the identification data. This can be an anonymization unit for automatic creation of the code from identification data of a patient for example. The anonymization can in particular be done according to a predetermined table, a predetermined algorithm or a predetermined function.
- a data interface designed for sending of medical patient data and the associated code from the first (medical) network area to a server (e.g. a cloud service). This network interface should fulfill particular security requirements, as must typically occur in communication of a medical network with a network to be regarded as insecure.

An inventive medical system (or device), of at least one embodiment, especially in the form of a system (device) of the group PACS, RIS, HIS ("Hospital Information System"), EMR, medical measuring system, medical imaging system and therapy planning system, comprises an inventive apparatus (and preferably also an inventive server system) or is designed to be incorporated into an inventive system.

Preferably the medical system of at least one embodiment is embodied for carrying out the method steps of the inventive method, which do not execute in or are executed by the server (e.g. the cloud service). These are:

Provision of medical patient data,

Provision of identification data for identification of the patient,

Provision of a code, which is linked to the identification data,

Sending of medical patient data and the associated code from the first (medical) network area to a server (e.g. a cloud service) in the second (NoPHI) network area, Provision of identification data or input of identification data for identification of a patient by a user, Establishing of a code linked to this identification data, Automatic sending of the code to the server (e.g. the cloud service).

To this extent, at least one embodiment is also a directed to a corresponding computer program product with a computer program, which is able to be loaded directly into a processing system or a network component, with program sections for carrying out all steps of an embodiment of the inventive method when the program is executed in the processing system or the network component. Such a computer program product, as well as the computer program, might possibly comprise additional elements such as e.g. documentation and/or additional components including hardware components, such as e.g. hardware keys (dongles etc.) for using the software.

For transport to the computer system or to the network component and/or for storage on or in the computer system or the network component a computer-readable medium, e.g. a memory stick, a hard disk or any other transportable or permanently-installed data medium can be used, on which the program sections of the computer program able to be read in and executed by a computer system are stored. To this end the processing unit can have, for example, one or more microprocessors or the like working together.

At least one embodiment is directed to a method for data communication in a network with a first network area and a second network area, to which, according to specification, patient data is sent anonymized, the method comprising:

provisioning medical patient data;

provisioning identification data for identification of a patient;

provisioning an associated code, linked to the identification data;

sending the medical patient data and an associated code from the first network area to a server in the second network area;

processing the medical patient data a cloud service;

provisioning second identification data or receiving input of identification data for identification of a patient by a user;

establishing of a code linked to the second identification data;

automatically sending the code established to the server;

establishing a status of the processing of patient data linked to the code established, and creating a corresponding status notification at the server; and sending the corresponding status notification from the server to the user.

At least one embodiment is directed to a method for data communication in a network including a first network area and a second network area, to which, according to specification, patient data is sent anonymized, the method comprising:

provisioning medical patient data;

provisioning identification data for identification of a patient;

provisioning an associated code, linked to the identification data;

sending the medical patient data and an associated code from the first network area to a server in the second network area;

provisioning second identification data or receiving input of identification data for identification of a patient by a user;

establishing a code linked to the second identification data;

automatically sending the code established to the server; and receiving a status notification of the server and forwarding the status notification to the user.

At least one embodiment is directed to a method for data communication in a network including a first network area and a second network area, to which, according to specification, patient data is sent anonymized, the method comprising:

receiving, at a server in the second network area, medical patient data and an associated code from the first network area;

processing the medical patient data by the server;

receiving a code sent by a user, at the server;

establishing a status of the processing of patient data linked to the code, and creating a corresponding status notification at the server; and sending the status notification established, to the user.

At least one embodiment is directed to a apparatus for data communication in a network including a first network area and a second network area, to which, according to specification, patient data is sent anonymized, the communication being based on medical patient data, identification data for identification of a patient and a code linked to the identification data, the apparatus comprising: an input interface, designed for entry of identification data for identification of a patient by a user; an identification unit, designed for establishing a code linked to the identification data; a data interface, designed for sending the code established to a server in the second network area; a data interface, designed for receiving a status notification of the server and for forwarding the status notification received to the user, wherein the apparatus is designed to communicate with a device or service in the medical network.

BRIEF DESCRIPTION OF THE DRAWINGS

The invention will be explained once again in greater detail below with reference to the enclosed figures on the basis of example embodiments. In the figures the same components are labeled with identical reference characters in different figures. As a rule the figures are not true-to-scale. In the figures.

DETAILED DESCRIPTION OF THE EXAMPLE EMBODIMENTS

Figure 1:
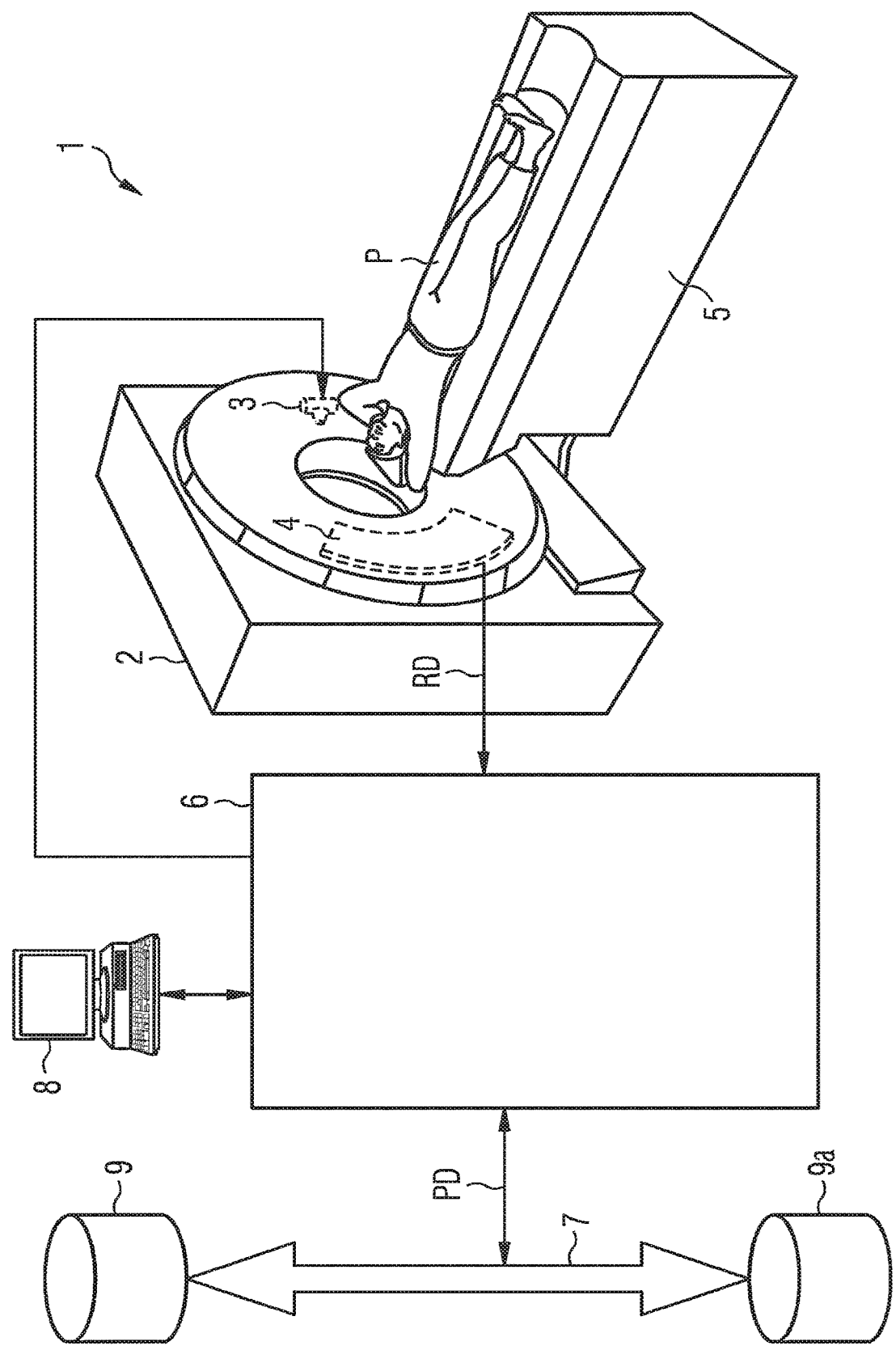
FIG. 1 shows a rough schematic diagram of a computed tomography system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between." "adjacent," versus "directly adjacent," etc.).

The terminology used herein is for the purpose of describing particular embodiments only and is not intended to be limiting of example embodiments of the invention. As used herein, the singular forms "a." "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising." "includes," and/or "including." when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term "circuit." The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the inventive method is used for data communication in a network, wherein this network comprises a first network area (this is a medical network area or a PHI network) and a second network area (this is a NoPHI network area, e.g. the Internet), to which, according to specification, patient data is sent anonymized. In the first (medical) network area patient data can be present as PHI data, since, according to specification, medical standards should apply there. In an embodiment, the method comprises: Provision of medical patient data, Provision of identification data for identifying the patient, and Provision of a code, which is linked to the identification data.

These steps first of all imply that this data must be available. Even if the data can theoretically originate from any location, it is especially preferred that it is initially available in a medical network as PHI data. This medical network can be the network of a hospital or of a medical practice for example. The data can be available there in particular in an RIS, a PACS, a medical device (e.g. a measuring device, an imaging system or another examination device).

Medical patient data is data about the medical state of the patient or is examination or measurement data. For example this patient data comprises images (or raw data for images) numerical and/or textual data about examinations (e.g. EEG or EKG data) or other medical data that is to be evaluated.

Identification data for identification of the patient is that data with which a patient can be identified. This data can comprise information from the group name, address, date of birth and a number (e.g. an identity card number). Even if the data can actually comprise data with which a patient is not so easy to identify (e.g. a sequence number or a file reference), this is not of primary importance here, since the identification data is to make a simple identification possible. Preferably the identification data is just information with which a direct identification of a patient is possible (e.g. as stated above: Data from the group name, address, date of birth and identity card number).

Anonymized identification data is referred to here as a "code". This code is linked for data processing to the identification data. This means in particular that the code represents encoded identification data. The code is this case must be constituted so that a reference back to identification data of a patient is uniquely possible and so that identical codes are also always created for the same identification data in each case. This can be achieved for example via a lookup table or a one-to-one function, as well as by a corresponding algorithm. The code serves to identify the data in a NoPHI area, so that, in the event of this data falling into the hands of unauthorized persons outside the medical network, said persons cannot recognize the patients to which this data is to be assigned. Preferably, after a code has been created, this is stored with the corresponding identification data in a database (e.g. as a table entry).

It should be noted that when a new (second) code is to be created from identification data from which a first code has been created, these two codes (essentially parts) must be identical or must at least make possible an identification of a data record in the cloud service, so that a patient can always be recognized correctly. This can be achieved for example by the same identification data of a patient always being encoded or anonymized in the same way, in order always to create the same code or a code with always identical parts (e.g. an identification part). However, before the code is created, there can always be a search in a predetermined table to see whether a code has already be created for the identification data, if it has been, this code can be used and if it hasn't a new code can be created and the information for it (e.g. identification data and code) written into the table.

It is pointed out at this juncture that the code, which is created for the provision or entry of identification data, does not absolutely have to originate from the user or the system that provides this identification data (but can certainly originate from it). It is merely a matter of the cloud service receiving a code that it can assign to a data record for the corresponding patient. The code can thus also originate from an intermediate system (with an anonymizing unit, e.g. a lookup table). The codes (first code for marking the data and the second code after the user entry or provision) should have identical parts, so that a unique assignment to a data record in the cloud service can be undertaken, but they can also contain additional, not necessarily identical, information (such as e.g. a sequence number, a random number, or a hash value).

The patient data can be CT images of a patient for example, the identification data, name and date of birth of the patient and the code can be an alphanumeric code, which is linked via a lookup table to the patient.

Sending of medical patient data and the associated code from the first (medical) network area to a server (e.g. a cloud service) in the second (NoPHI) network area.

Of the aforementioned data provided, a number of data records, namely those that are to be processed by the server (e.g. a cloud service), are sent to the server. There the data is processed by a service provided by the server (e.g. said service in the cloud). A cloud service would include the servers of the cloud architecture. For the sake of greater clarity the text below also refers to "service", wherein this term always also includes the server as hardware. In precisely the same way "server" also includes the service that the server provides. The server is arranged in the second (No-PHI) network area.

A service on the server (e.g. a cloud service) can be the "AI-Rad Companion" service. This service is used for processing of patient data, in particular via artificial intelligence, but can also be a service based on conventional algorithms or a service in which an evaluation by humans takes place in the background. Naturally the code must be sent with the data, so that the processed patient data can be assigned to the correct patient later. The sending of the patient data together with the identification data does not come into question here, since the assumption is that the service is able to be reached via a NoPHI network (the second network area), i.e. lies in a network area, for which (e.g. according to applicable safety regulations) there can be no assumption of confidentiality or data security.

A cloud service (also referred to for short as a "cloud" below) is an IT infrastructure in which e.g. storage space or computing power and/or application software is made available via a network. Communication between the user and the cloud occurs in such cases via data interfaces and/or data transmission protocols. In the present case the particular preference is for the cloud service to make both computing power and application software available.

Within the framework of one preferred method patient data is provided via the network to the cloud service. This comprises a computer system, e.g. a computer cluster, which does not generally include the local computer of the user. This cloud can in particular be made available by the medical facility that also provides the medical technology system. For example the data in a recorded image is sent via an RIS or PACS to a (remote) computer system (the cloud). Preferably the computer system of the cloud, the network and also the medical system represent a virtual network in the data processing sense. The method can be realized in this case via a set of commands in the network. The data processed in the cloud ("result data") will be sent via the network again later to the local computer of the user (see below).

On the server side there is then a processing of the patient data by the server (e.g. the cloud service).

The server or the service now processes the patient data according to predetermined conditions. This can be an evaluation of images and the marking of regions of interest in these images for example. Processed patient data is created, which is also referred to below as "result data". This processing is the reason for which the data is sent to the server (e.g. to a cloud service) at all.

Provision of Identification Data or Input of Identification Data for Identification of a Patient by a User.

A patient is now specified directly here by a user. For example the name (or other data) of the patient is entered into a search mask. Even if it could be theoretically possible, no data similar to a code should be entered in this step, but rather identification data that allows the patient to be deduced directly. This step can also be automated, e.g. through specific guidelines and user administration measures (e.g. the "Active Directory" service could be used for this). Active Directory is a user authentication (login) for medical personnel. It guarantees that only authorized users gain access to the cloud service. Medical personnel can also search for a patient directly, but in practice the appropriate code would have to be created by the user system, if this were not taken care of by a central facility (see above). If the user system (or user themselves) do not know the code, the generation of the code can be carried out automatically via Active Directory, as described in greater detail above for example, by a central anonymization unit in the medical network being used for example.

Establishing a Code Linked to this Identification Data.

The identification data should not be sent to the second network area. The service could not do anything with this identification data, since it only has codes available to it. Therefore the identification data must initially be encoded as a code. This is done according to the same principle as the one by which the aforementioned codes have been established (see above). In such cases each patient always has the same code. This can be achieved in this case for example by the identification data specified here being compared with the previously mentioned identification data (e.g. via a lookup table) and by the code matching the above mentioned code relating to this data being used here. If there is no match, the code can be an empty set or an error code. Naturally it is also possible to establish the code from the identification data via a predetermined function or via a predetermined algorithm, wherein the same function or the same algorithm is used as for the above-mentioned code, so that the same code is always created for each patient.

Automatic Sending of the Code to the Server (e.g. the Cloud Service).

The code is now sent via the network to the server or the service.

On the server side there is now an establishing of the status of the processing of patient data linked to this code, and creation of a corresponding status notification by the server (e.g. the cloud service).

Since the server or the service has received the patient data for processing together with the code, it is a simple matter to establish what the processing status of the patient data concerned is. Basically there are a clear number of possibilities, namely e.g.: "not available", "not yet processed", "processing in progress" (possibly with a specification of the progress or of the amount processed), "processing completed" and "error during processing". The status notification can contain an alphanumeric code, to which a notification can be assigned by default, the status notification can however also contain a text, e.g. one of the status messages given above.

After the status has been established, on the server side there is a sending of the status notification to the user.

The status notification is sent via the network to the user in this case.

Receiving of a Status Notification (S) of the Server (AI) and Forwarding of the Status Notification (S) to the User.

The status message sent by the server is received on the user side and preferably displayed to the user (possibly after assignment of an alphanumeric code of the status notification to a default notification). Preferably in this case the code is again assigned to the identification data of the patient, so that the user immediately knows the patient for which this is the status notification (e.g. if a number of patients have been queried at the same time).

For security reasons it is preferred that before this step (but preferably even before the input mentioned above) a user identification is undertaken, so that no unauthorized persons can view patient data. The user identification can be undertaken on access to the network, during input of identification data or within the framework of the step mentioned here. It is of advantage if, even in the event of the clinical data being present anonymized on the server (e.g. in the cloud), care is still taken that no unauthorized parties gain access to it.

For the same reason the entire communication should be undertaken encrypted, provided the entire network is safely protected from unauthorized access. Communication should at least be undertaken encrypted where third parties can have access to the data.

An inventive (user-side) method of at least one embodiment for data communication in a network with a first network area and a second network area, to which, according to specification, patient data is sent anonymized, can work hand-in-hand with the server-side method described below. So that data is processed anyway and a corresponding notification can be created anyway, the following steps should be performed beforehand:

Provision of medical patient data,

Provision of identification data for identification of a patient,

Provision of a code, which is linked to the identification data,

Sending of medical patient data and the associated code from the first network area to a server in the second network area (and naturally processing of the patient data by the server).

These steps can also occur within the framework of the (user-side) method, but this is not absolutely necessary however, e.g. if the user is accessing the server via a terminal from outside (from outside the first (medical) network. It should also be mentioned once again for the sake of clarity that the user does not absolutely have to be located in the first (medical) network, but that this is preferable.

The (user-side) method of at least one embodiment comprises the following steps:
  Provision of identification data or input of identification data for identification of a patient by a user,
  Establishing of a code linked to this identification data,
  Automatic sending of the code to the server,
  Receiving of a status notification of the server and forwarding of the status notification to the user.

An inventive (server-side) method of at least one embodiment for data communication in a network with a first network area and a second network area, to which, according to specification, patient data is sent anonymized, which can work hand-in-hand with the user-side method stated above, comprises the following steps:
  Receiving of medical patient data and an associated code from the first network area by a server in the second network area,
  Processing of the patient data (which has been sent above to the server) by the server,
  Receiving of a code sent by a user by the server,
  Establishing of the status of the processing of patient data linked to this code, and creation of a corresponding status notification by the server, and
  Sending of the status notification to the user.

The inventive apparatus of at least one embodiment is used for data communication in a network with a first (medical) network area and a second (NoPHI) network area, to which, according to specification, patient data is sent anonymized. In this case communication is based on medical patient data, identification data for identification of the patient and a code linked to the identification data. The apparatus comprises the following components:
  An input interface designed for entry of identification data for identification of a patient by a user. This can be a keyboard for example, but can also be a terminal.
  An identification unit designed for establishing a code linked to this identification data. This identification unit should have access to that component, which creates a code from identification data or a module for creating a code from identification data as described above within the framework of the method.
  A data interface designed for sending the code to the server (e.g. the cloud service). This can be a normal, well-known data interface, in particular such as is used for communication from a medical network.
  A data interface designed for receiving a status notification of the server (e.g. of the cloud service) and for forwarding the status notification to the user. This can be a normal, well-known data interface, in particular such as is used for communication from a medical network. In particular it is the same data interface as that described above, which is designed for bidirectional communication.

The apparatus is designed in at least one embodiment to communicate with a device or service in the medical network.

The apparatus is preferably embodied for executing steps of the inventive (user-side) method, which are performed within the medical networks and/or on the user's system.

A corresponding inventive server system of at least one embodiment for data communication in a network with a first network area and a second network area, to which, according to specification, patient data is sent anonymized, which can work hand-in-hand with the (user-side) method stated above, comprises the following components:

Receiving of medical patient data and an associated code from the first network area sent to a server in the second network area,
  Processing of the patient data (which has been sent above to the server) by the server,
  Receiving by the server of a code sent by a user,
  Establishing of the status of processing of patient data linked to this code, and creation of a corresponding status notification by the server, and
  Sending of the status notification to the user.

An inventive system of at least one embodiment for data communication comprises the following components:
  A network comprising a first (medical) network area and a second (NoPHI) network area, to which, according to specification, patient data is sent anonymized.
  A unit designed for provision of medical patient data, of identification data for identification of the patient. This unit can be a PACS or a medical imaging system and/or an RIS for example.
  A unit designed for provision of a code, which is linked to the identification data. This can be an anonymization unit for automatic creation of the code from identification data of a patient for example. The anonymization can in particular be done according to a predetermined table, a predetermined algorithm or a predetermined function.
  A data interface designed for sending of medical patient data and the associated code from the first (medical) network area to a server (e.g. a cloud service). This network interface should fulfill particular security requirements, as must typically occur in communication of a medical network with a network to be regarded as insecure.

An inventive apparatus and preferably also an inventive server system are disclosed.

An inventive medical system (or device), of at least one embodiment, especially in the form of a system (device) of the group PACS, RIS, HIS ("Hospital Information System"), EMR, medical measuring system, medical imaging system and therapy planning system, comprises an inventive apparatus (and preferably also an inventive server system) or is designed to be incorporated into an inventive system.

Preferably the medical system of at least one embodiment is embodied for carrying out the method steps of the inventive method, which do not execute in or are executed by the server (e.g. the cloud service). These are:
  Provision of medical patient data,
  Provision of identification data for identification of the patient,
  Provision of a code, which is linked to the identification data,
  Sending of medical patient data and the associated code from the first (medical) network area to a server (e.g. a cloud service) in the second (NoPHI) network area,
  Provision of identification data or input of identification data for identification of a patient by a user,
  Establishing of a code linked to this identification data,
  Automatic sending of the code to the server (e.g. the cloud service).

A large part of the components of the apparatus or of the server system previously mentioned or of the system (in particular the aforementioned method steps, which do not execute in or are executed by the server, e.g. the cloud service), can be realized entirely or in part in the form of software modules in a processor of a corresponding apparatus or of a server system or in a system. A largely software-based realization has the advantage that even apparatuses or systems previously used can be upgraded in a simple manner by a software update, in order to work in the inventive way.

To this extent, at least one embodiment is also a directed to a corresponding computer program product with a computer program, which is able to be loaded directly into a processing system or a network component, with program sections for carrying out all steps of an embodiment of the inventive method when the program is executed in the processing system or the network component. Such a computer program product, as well as the computer program, might possibly comprise additional elements such as e.g. documentation and/or additional components including hardware components, such as e.g. hardware keys (dongles etc.) for using the software.

For transport to the computer system or to the network component and/or for storage on or in the computer system or the network component a computer-readable medium, e.g. a memory stick, a hard disk or any other transportable or permanently-installed data medium can be used, on which the program sections of the computer program able to be read in and executed by a computer system are stored. To this end the processing unit can have, for example, one or more microprocessors or the like working together.

Further especially advantageous embodiments and developments of the invention emerge from the dependent claims as well as from the description given below, wherein the claims of one claim category can also be developed analogously to the claims and parts of the description into another claim category and in particular individual features of different example embodiments or variants can also be combined into new example embodiments or variants.

In accordance with a preferred method the processed patient data (result data) is sent from the server (e.g. the cloud service) to the user with or after the sending of the status notification to the user. The user can receive the result data automatically (even together with the status notification), however it is preferred that the user receives the result data after an interaction on their part, e.g. after a query, a confirmation or a click on a link.

Thus on the user side, preferably with or after the status notification is received, corresponding result data is received (which was sent from the server to the user), in particular after an interaction by the user.

The user can then check the result data and then store the checked result data in a device in the medical network. The processed patient data received is thus sent to a device in the medical network, in particular a PACS or RIS. The data is stored in such cases preferably after an interaction by the user (e.g. a confirmation).

In accordance with a preferred method the medical patient data and the code are sent from the medical network to the server (e.g. the cloud service), preferably from a medical (imaging) system, a PACS, an RIS, a HIS, an EMR and/or a therapy planning system. In this form of embodiment it is insured that the patient data originates from that medical facility to which the medical network belongs or from stations connected to the medical network.

In accordance with one preferred method the user accesses the medical network via a device and/or a software application, e.g. a PACS viewer. Communication between server (e.g. the cloud service) and user occurs in such cases via the medical network. This insures that communication takes place exclusively via the medical network and there cannot be access from a random location via the internet directly to the server (e.g. the cloud service).

In accordance with one preferred method communication between the first (medical) network area and the server (e.g. the cloud service) is encrypted and is preferably undertaken via software for remote access to software applications, e.g. the "VPN" or "teamplay" software. In this case there is preferably an in particular encrypted communication between the user and the server (e.g. the cloud service) especially preferably via software for remote access to software applications. A user thus first logs into the medical network. Such an encryption should preferably be accompanied by a user authentication. Even if the patient has been anonymized by the code such an encryption has important advantages. In this way an effective encryption can effectively prevent or uncover impermissible access to the patient data, for example, from people attacking the data stream (man in the middle).

In accordance with one preferred method the establishment of a code on the basis of identification data is undertaken via a lookup table, an algorithm or a unique function. It is emphasized once again here that only a single code may be available for each patient. This should always be created when the identification data of this patient is entered or provided for a transmission to the server (e.g. the cloud service). Thus the code both for sending the patient data to the service and also during later entry or provision of the identification data should use the same method for creating the code from identification data.

In accordance with one preferred method the status notification comprises information about the status of processing by the server (e.g. the cloud service). As stated previously, this can be an alphanumeric code or a textual notification, e.g. "data not available", "being processed", "done", "error". In the event of processing of the patient data having finished the status notification preferably additionally contains information about a result. For example in the evaluation of a CT image it can be specified which anomalies or pathologies have been found. It is preferred that these results are given in the form of a summary of the most important points. The status notification is especially preferably output to the user, in particular in the form of a standardized representation.

It is preferred that the status notification additionally comprises data that specifies the type or the format of the representation, e.g. the size of the output window, the background and/or font color, the font size or data for acoustic effects. Even if the output per se can be programmed at the user system, e.g. in the form of a specification in a program or an App, it is preferred that there is access to output objects in the operating system or libraries of the user system or to presentation functions in a PACS or RIS, which are formatted with the additional data.

A preferred apparatus comprises an anonymization unit for automatic creation of the code from identification data of a patient, in particular according to a predetermined table, a predetermined algorithm or a predetermined function. Even if it is conceivable that with a sufficient encryption of the data, an anonymization does not take place, this involves security concerns however. In order to guarantee with certainty that a manual re-identification of the patient cannot be carried out by unauthorized third parties, the anonymization and re-identification must be undertaken so that this cannot be viewed from outside. Therefore the code is created by an anonymization unit, which especially preferably is positioned in the medical network.

Preferably the sending of the data to be processed to the server (e.g. the cloud service) is initiated or controlled by the apparatus. As an alternative or in addition it is possible, in the network or the apparatus, to apply an application (a program), which controls the network traffic (e.g. "VPN", "teamplay", in particular the "teamplay_Receiver") and acts as a transfer mechanism to the service. This program can readily run on another physical computer unit from other components of the apparatus. It would also be conceivable, above all in small clinics and medical practices, for the software components of the apparatus to run on a single computer.

In a preferred apparatus the device or the service in the medical network is a service or device of the group PACS, RIS, HIS, EMR, medical measuring system, medical imaging system and therapy planning system.

A preferred system is designed for the apparatus to communicate with the server (e.g. the cloud service) via the medical network. To do this it is preferred that the apparatus (or the user working at the apparatus) first of all logs into the medical network.

It is preferred that the system or the method is designed to predetermine a geographically-defined forwarding of the data sent via the network and/or only to send data to a clearly-defined set of servers. This serves to comply with possible legal regulations that forbid medically-relevant data going beyond national boundaries. For example the system comprises a positive list of network interfaces (e.g. routers and/or servers), to which data may be sent and is especially preferably designed so that no data can be sent to other network services. The same applies for a preferred method. As well as the use of the positive list described above the possibilities of geoblocking and/or of response time measurement are also preferred.

One problem in practice can be finding the computer system to which the status notification is to be sent. In a clinical environment there occasionally exist many smaller networks, which are separated from one another by firewalls or other security mechanisms. Although the service itself has a code, it does not know from which computer this code has been sent. Therefore it is preferred that, together with the code, a token is sent from the user (the computer unit, at which the user has logged in) to the service and is sent back together with the status notification. Such a token is also referred to here, for better identification, as a "service token". The medical network in this case comprises an element, e.g. a proxy server or a router, that can assign this token to the user and sends a status notification as a function of the token enclosed with it to a specific station in the medical network (the computer of the user). The same applies for the result data for a specific code.

It should be noted that the user system (e.g. a terminal) is meant by the term "user", since only the user system is relevant for the network.

In practice it is quite possible to work with a number of tokens. For example a few network applications (such as e.g. teamplay) use tokens that are activated by an authentication and lose their validity after a certain period of inactivity. These tokens are used for communication with the corresponding service. It is preferred that the service token has a validity independent of such an "application-based token", which is appropriate for working with the service, e.g. a validity of at least half an hour or at least one hour and/or a maximum of eight hours. The system in this case is designed so that data with the service token can pass through the network from the service to the user's computer independently of other tokens and especially preferably also data from the user's computer to the service.

FIG. 1 shows a rough schematic of a computed tomography system 1 with a control facility 6 for creation of image data, which is seen here as an example for patient data. The computed tomography system 1, in the usual way, has a scanner 2 with a gantry, in which an x-ray source 3 rotates, which irradiates a patient in each case, who is pushed via a couch 5 into a measurement space of the gantry, so that the radiation strikes a detector 4 lying opposite the x-ray source 3 in each case.

The control facility 6 obtains raw data from the scanner 2, reconstructs image data from this raw data and forwards this image data as patient data PD to a data bus 7. An operator can operate the control facility 6 and thus the computed tomography system 1 via a terminal 8.

The data bus 7 makes possible a connection to an RIS 9a (Radiology Information System) or PACS 9 (Picture Archiving and Communication system). The data bus can however also establish a connection to a network component in a medical network, by which the patient data PD (together with a code K) can be sent to a cloud service AI (see also the figures below for more information), which in these examples represents a preferred example embodiment for a server AI or service and indeed can also be seen in general terms as server AI.

Figure 2:
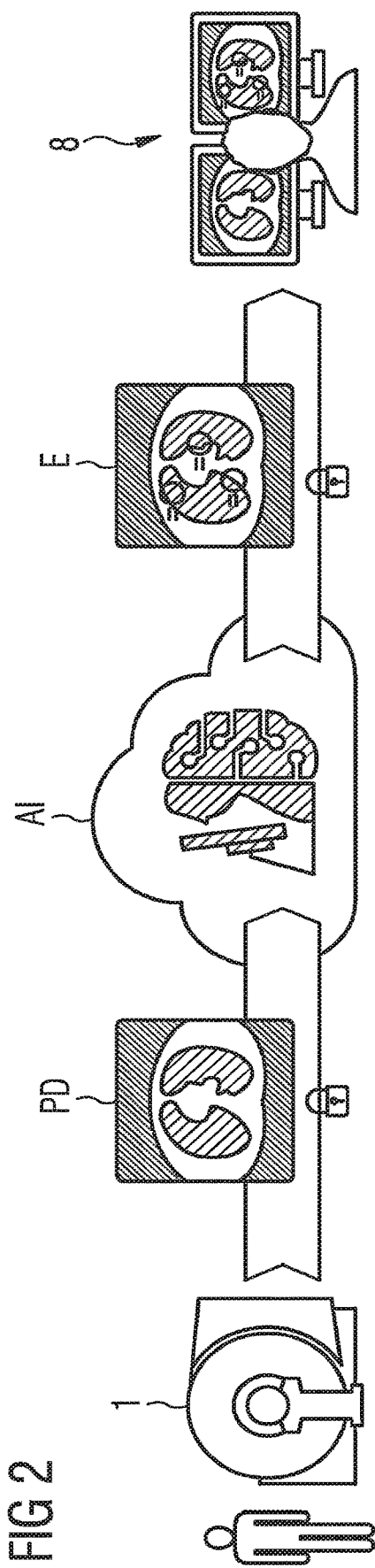
FIG. 2 shows a rough schematic diagram of the processing of data by a cloud service.

FIG. 2 shows a rough schematic diagram of the processing of patient data PD by a cloud service AI. In this example the patient data PD is sent from a medical imaging system 1, here a computed tomography system 1 for example, to the cloud service AI, is processed there and the Result data E (the processed patient data) is sent to a user or to their computer system. This computer system can for example be the terminal 8 with its display unit 8 shown in FIG. 1, which in addition to controlling the CT system 1, could also serve as a diagnostic system. The padlocks below the arrows, which are intended to represent the flow of data, stand for an encryption of data communication, which is especially preferred.

Figure 3:
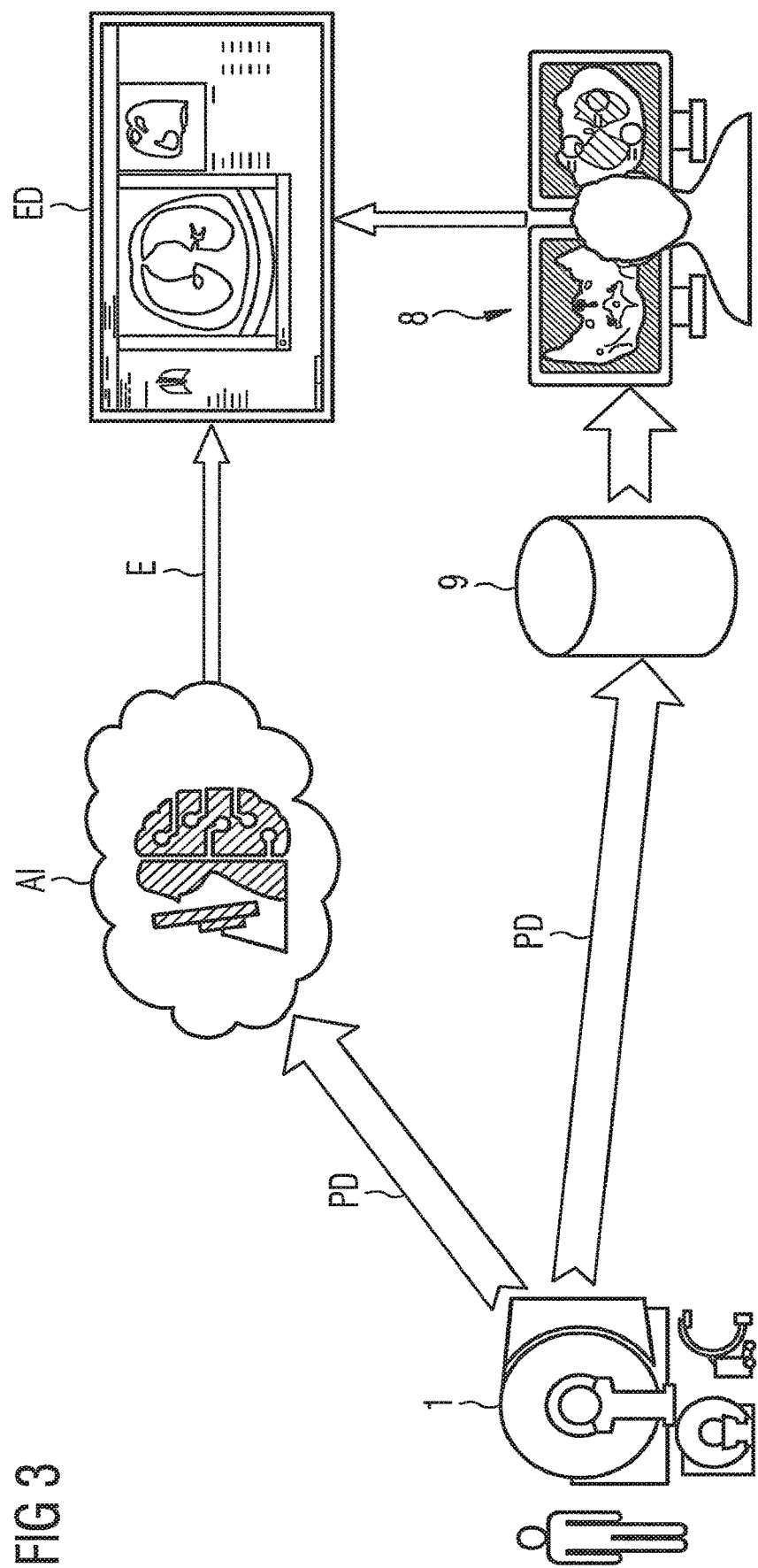
FIG. 3 shows a rough schematic diagram of the processing of data by a cloud service.

FIG. 3 shows a rough schematic of the processing of patient data PD by a cloud service AI, which is intended to illustrate the problem underlying the invention. In this example too the patient data PD is sent from a medical imaging system 1 to the cloud service AI, but at the same time also to a PACS 9. The cloud service AI (data flow indicated by arrows). The cloud service AI may not automatically store its result data in the PACS 9 here however, so that this must be assessed separately for the PACS by a user at a terminal 8. This user accesses an external service ED (seen from the PACS) and assesses the data there. A notification about the status of the processing of the patient data from the external service ED is problematic. Moreover problems in the area of security can occur.

Figure 4:
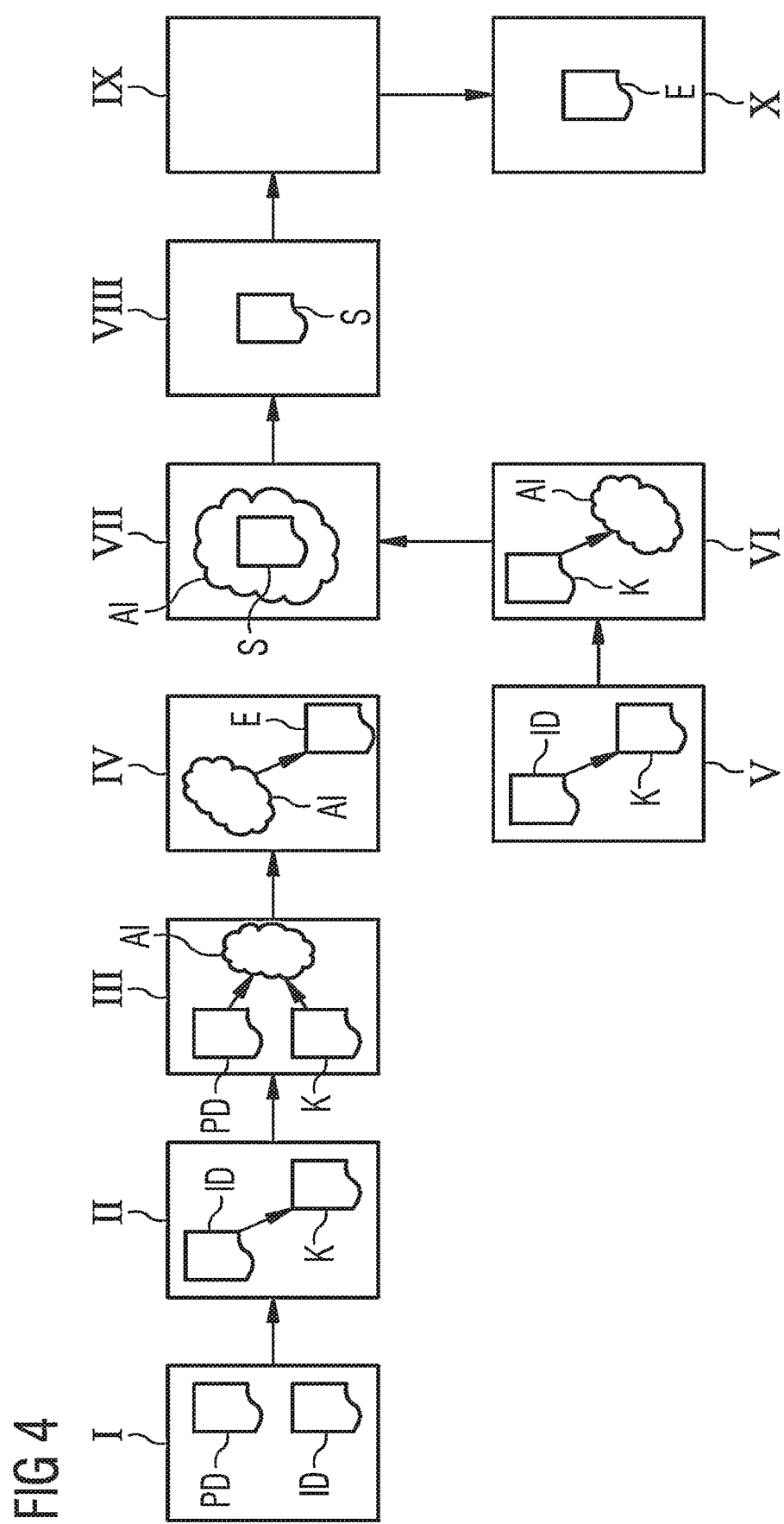
FIG. 4 shows a schematic of an example embodiment of the inventive method.
Figure 5:
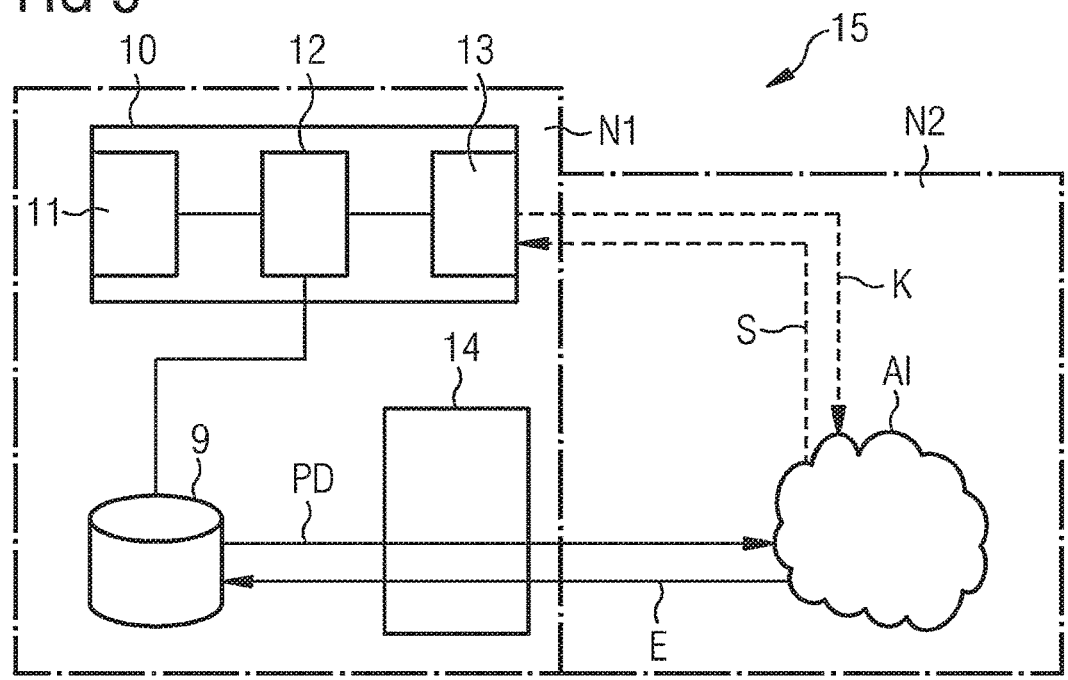
FIG. 5 shows a schematic of an example embodiment of the inventive system with an inventive apparatus.
Figure 6:
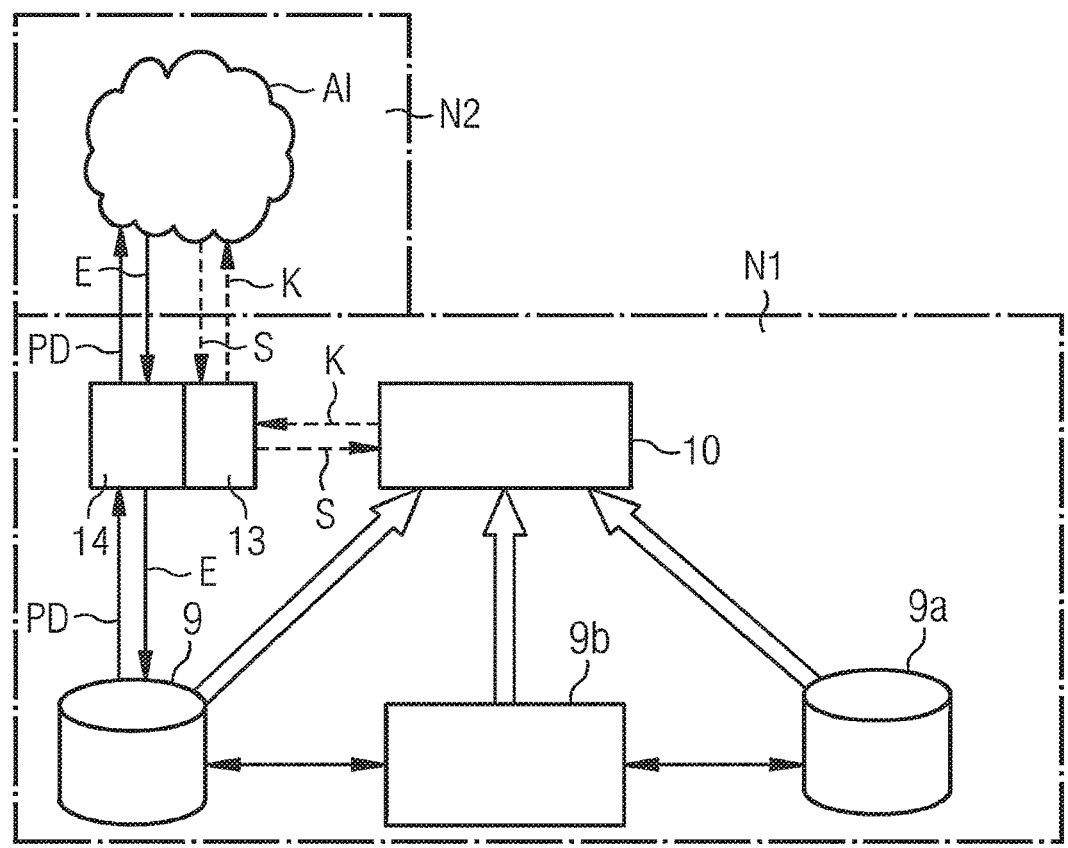
FIG. 6 shows a schematic of an example embodiment of a practical implementation of the inventive method.

FIG. 4 shows a schematic example embodiment of the inventive method for data communication in a network with a first (medical) network area N1 and a second (NoPHI) network area N2 to which, according to specification, patient data PD is sent anonymized (see also FIGS. 5 and 6 in this connection).

In step I there is provision of medical patient data and identification data ID for identification of the respective patient P.

In step II a code K linked very closely to this data is created from the identification data ID, by which a reversible anonymization of the identification data ID is possible.

In step III there is sending of medical patient data PD and the associated code K in each case from the first (medical) network area N1 to a (cloud) service AI in the second (NoPHI) network area N2.

In step IV the patient data PD received by the cloud service AI is processed by said service and result data E is created. This Result data E is naturally still linked to the respective code K, so that later an assignment to the corresponding patient P is possible.

In step V there is provision of identification data ID or input of identification data ID for identification of a patient P by a user. This can be done before, during or after the processing of patient data PD by the cloud service AI.

In step VI a code K is established from this identification data ID, which is always identical for the same identification data ID. This code K is subsequently sent automatically to the cloud service AI.

In step VII there is an establishment of the status of the processing of patient data PD linked to this code K, and creation of a corresponding status notification S by the cloud service AI.

In step VIII the status notification S is sent to the user.

In step IX there is an interaction by the user for receiving the result data, e.g. a confirmatory mouse click on a corresponding button or a link on the screen.

In step X the result data E is then sent from the cloud service AI to the user for assessment. After assessing it, said user can store the result data E in a device in the medical network N1, e.g. in a PACS 9. This can be image data automatically provided with markings (sent from the cloud service) and viewed by an assessor in a browser window for example.

FIG. 5 shows a schematic example embodiment of the inventive system 15 for data communication with an inventive apparatus 10. The figure shows a network with a first (medical) network area N1 and a second (NoPHI) network area N2. Patient data PD may only be sent anonymized, according to specification, to the second (NoPHI) network area (with a code K). In this network an inventive communication should take place, as has been described in greater detail in FIG. 4 for example. Data flows are shown by arrows.

The system 15 comprises a unit designed for provision of medical patient data PD and of identification data ID for identification of a patient P. This unit is shown here in the form of a PACS 9.

The system 15 also comprises a network interface 14, which is used for communication with the cloud service. This means that the network interface 14 functions as a data interface for sending medical patient data PD and the associated code K from the first (medical) network area N1 to the cloud service AI.

Shown at the top in the medical network N1 is an apparatus 10, which has an input interface 11, an identification unit 12 and a data interface 13.

The input interface 11 is designed for entry of identification data ID for identification of a patient by a user. Theoretically the terminal 8 from FIG. 1 could also be used as the input interface 11.

The identification unit 12 is designed to establish a code K linked to this identification data ID. Since a code must be linked uniquely with the identification data ID, the identification unit 12 can be used at the same time as an anonymization unit 12. In the example shown here the identification unit 12 simultaneously serves as an anonymization unit 12, or as a unit designed for provision of a code K, which is linked to the identification data ID of patient data PD to be sent.

The data interface 13 is designed for sending of the code K to the cloud service. At the same time the data interface 13 is also designed for receiving a status notification S of the cloud service AI and for forwarding the status notification S to the user. The network interface 14 could also theoretically be used as the data interface 13.

The apparatus 10 communicates in the example shown via the network interface 14 from the first (medical) network area N1 with the cloud service AI.

FIG. 6 shows a schematic example embodiment of a practical implementation of the inventive method. The architecture is similar to that shown in FIG. 5, with the difference that the network interface 14 (e.g. a "teamplay Receiver" has a particular network service (for example a particular plug-in for teamplay) as its data interface 13, with which the apparatus 10 communicates with the cloud service AI.

While only one device (a PACS 9) is shown in FIG. 5 in the medical network N1, three devices are present here, a PACS 9, from which the patient data PD is sent to the cloud service AI, an RIS 9a and a data processing device 9b. As an alternative a data record can also be sent directly from a CT scanner for example (see e.g. FIG. 1). As is indicated by the outlined arrows pointing from the devices to the apparatus 10, the apparatus 10 can receive information of the devices here. For example the apparatus 10 can receive from the PACS 9 notes about the data sent to the cloud service AI or information about a change of patient. From the RIS 9b the apparatus 10 can obtain information about which patient P is the next to be retrieved for an impending assessment of the automatically evaluated data. From the data processing unit 9b the apparatus 10 can obtain more detailed information about the corresponding identification data ID.

In conclusion it is pointed out once again that the method described in detail above as well as the system shown merely involve example embodiments, which can be modified by the person skilled in the art in a wide variety of ways, without departing from the area of the invention. Furthermore the use of the indefinite article "a" or "an" does not exclude the features concerned also being able to be present more than once. Likewise the terms "unit" and "module" do not exclude the components concerned consisting of a number of interoperating subcomponents, which where necessary can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for data communication in a network including a first network area and a second network area, the method comprising:
receiving medical patient data of a patient from the first network area;
receiving an associated code linked to first identification data identifying the patient within the first network area;
receiving a code linked to second identification data, the second identification data being identification data for identifying the patient within the first network area;
establishing a status of processing of the medical patient data of the patient in response to selecting the medical patient data of the patient based on the associated code and the code linked to the second identification data; and
sending a status notification indicating the status of the processing of the medical patient data of the patient to a user.

2. The method of claim 1, further comprising:
processing the medical patient data independent of the first identification data.

3. The method of claim 1, further comprising:
sending processed medical data to the user with or after the sending of the status notification to the user.

4. The method of claim 1, wherein
the status notification includes the status of the processing of the medical patient data, and
the status notification is output to the user in a standardized representation in response to the processing of the medical patient data being complete.

5. The method of claim 1, wherein the code linked to the second identification data matches the associated code.

6. The method of claim 1, wherein the code linked to the second identification data includes an identification part that matches an identification part of the associated code.

7. The method of claim 1, wherein the method is performed by a server in the second network area.

8. A non-transitory computer-readable medium storing executable instructions that, when executed by a computer, cause the computer to perform
receiving medical patient data of a patient from a first network area;
receiving an associated code linked to first identification data identifying the patient within the first network area;
receiving a code linked to second identification data, the second identification data being identification data for identifying the patient within the first network area;
establishing a status of processing of the medical patient data of the patient in response to selecting the medical patient data of the patient based on the associated code and the code linked to the second identification data; and
sending a status notification indicating the status of the processing of the medical patient data of the patient to a user.

9. A system for data communication in a network including a first network area and a second network area, the system comprising:
at least one memory configured to store instructions; and
at least one processor configured to execute the instructions and cause the system to perform
receiving medical patient data of a patient from the first network area,
receiving an associated code linked to first identification data identifying the patient within the first network area,
receiving a code linked to second identification data, the second identification data being identification data for identifying the patient within the first network area,
establishing a status of processing of the medical patient data of the patient in response to selecting the medical patient data of the patient based on the associated code and the code linked to the second identification data, and
sending a status notification indicating the status of the processing of the medical patient data of the patient to a user.

10. A method for data communication in a network including a first network area and a second network area, the method comprising:
providing medical patient data of a patient within the first network area;
providing first identification data for identification of the patient within the first network area;
providing an associated code linked to the first identification data within the first network area;
sending the medical patient data and the associated code from the first network area to a server in the second network area;
providing second identification data or receiving the second identification data for identification of the patient by a user within the first network area;
establishing a code linked to the second identification data within the first network area;
sending, to the server, the code linked to the second identification data; and
receiving a status notification from the server corresponding to a status of a processing of the medical patient data of the patient in response to selecting the medical patient data of the patient at the server based on the associated code and the code linked to the second identification data.

11. The method of claim 10, wherein the associated code provides a reference back to the first identification data.

12. The method of claim 10, wherein the providing an associated code linked to the first identification data within the first network area includes creating the associated code from the first identification data of the patient.

13. The method of claim 10, wherein the code linked to the second identification data is established based on the second identification data using at least one of a lookup table, an algorithm or a unique function.

14. The method of claim 10, further comprising:
receiving processed medical data from the server with or after the receiving of the status notification from the server.

15. The method of claim 10, wherein
the first network area is a medical network,
the medical network is accessible by the user via at least one of a device or a software application, and the server and the user communicate via the medical network.

16. The method of claim 10, wherein
the status notification includes the status of the processing of the medical patient data at the server, and
the status notification is output to the user in a standardized representation.

17. The method of claim 10, wherein the code linked to the second identification data matches the associated code.

18. The method of claim 10, wherein the code linked to the second identification data includes an identification part that matches an identification part of the associated code.

19. A non-transitory computer-readable medium storing executable instructions that, when executed by a computer, cause the computer to perform
   providing medical patient data of a patient within a first network area;
   providing first identification data for identification of the patient within the first network area;
   providing an associated code linked to the first identification data within the first network area;
   sending the medical patient data and the associated code from the first network area to a server in a second network area;
   providing second identification data or receiving the second identification data for identification of the patient by a user within the first network area;
   establishing a code linked to the second identification data within the first network area;
   sending, to the server, the code linked to the second identification data; and
   receiving a status notification from the server corresponding to a status of a processing of the medical patient data of the patient in response to selecting the medical patient data of the patient at the server based on the associated code and the code linked to the second identification data.

20. A system for data communication in a network including a first network area and a second network area, the system comprising:
   at least one memory configured to store instructions; and
   at least one processor configured to execute the instructions and cause the system to perform
      providing medical patient data of a patient within the first network area,
      providing first identification data for identification of the patient within the first network area,
      providing an associated code linked to the first identification data within the first network area,
      sending the medical patient data and the associated code from the first network area to a server in the second network area,
      providing second identification data or receiving the second identification data for identification of the patient by a user within the first network area,
      establishing a code linked to the second identification data within the first network area,
      sending, to the server, the code linked to the second identification data, and
      receiving a status notification from the server corresponding to a status of a processing of the medical patient data of the patient in response to selecting the medical patient data of the patient at the server based on the associated code and the code linked to the second identification data.

21. A server for data communication in a network including a first network area and a second network area, the server being in the second network area and comprising:
   one or more processors; and
   a memory storing computer-executable instructions that, when executed by the one or more processors, cause the server to
      receive medical patient data of a patient from the first network area,
      receive an associated code linked to first identification data identifying the patient within the first network area,
      receive a code linked to second identification data, the second identification data being identification data for identifying the patient within the first network area,
      establish a status of processing of the medical patient data of the patient in response to selecting the medical patient data of the patient based on the associated code and the code linked to the second identification data, and
      send a status notification to a user.

* * * * *